(12) United States Patent
Flaherty et al.

(10) Patent No.: US 7,186,869 B2
(45) Date of Patent: Mar. 6, 2007

(54) PURIFICATION OF SATURATED HALOCARBONS

(75) Inventors: Stephen Andrew Flaherty, Moroton (GB); Paul Hendry Stewart, South Wirral (GB)

(73) Assignee: Ineos Fluor Holdings Limited (GB)

( * ) Notice: Subject to any disclaimer, the term of this patent is extended or adjusted under 35 U.S.C. 154(b) by 513 days.

(21) Appl. No.: 10/473,294

(22) PCT Filed: Mar. 28, 2002

(86) PCT No.: PCT/GB02/01544

§ 371 (c)(1), (2), (4) Date: Feb. 5, 2004

(87) PCT Pub. No.: WO02/079129

PCT Pub. Date: Oct. 10, 2002

(65) Prior Publication Data

US 2004/0133051 A1    Jul. 8, 2004

(30) Foreign Application Priority Data

Mar. 28, 2001  (GB) ................................ 0107705.6

(51) Int. Cl.
  *C07C 17/38*  (2006.01)
(52) U.S. Cl. ...................................... 570/177; 570/216
(58) Field of Classification Search ...................... None
  See application file for complete search history.

(56) References Cited

U.S. PATENT DOCUMENTS

| | | | |
|---|---|---|---|
| 2,999,885 A | 9/1961 | Heberling, Jr. | |
| 4,062,925 A | 12/1977 | Witenhafer et al. | |
| 4,129,603 A | 12/1978 | Bell | |
| 5,118,429 A | 6/1992 | Anderson et al. | |
| 5,430,203 A | 7/1995 | Dudman | |
| 5,696,310 A | 12/1997 | Jackson et al. | |
| 6,077,982 A | 6/2000 | Yates et al. | |

FOREIGN PATENT DOCUMENTS

| | | |
|---|---|---|
| CA | 2028879 A1 | 5/1992 |
| CA | 2074285 A1 | 1/1993 |
| DE | 233 839 A1 | 3/1986 |
| DE | 282 681 A5 | 9/1990 |
| EP | 0 357 328 A1 | 3/1990 |
| EP | 0 370 688 A1 | 5/1990 |
| EP | 0 457 613 A1 | 11/1991 |
| GB | 1067811 | 5/1967 |
| JP | 7-330640 | 6/1994 |
| RU | 2 088 563 C1 | 8/1997 |
| WO | WO 97/38958 | 10/1997 |
| WO | PCT/GB02/01544 | 10/2002 |
| WO | PCT/GB02/01544 | 6/2003 |

*Primary Examiner*—Sikarl A. Witherspoon
(74) *Attorney, Agent, or Firm*—Cook, Alex, McFarron, Manzo, Cummings & Mehler, Ltd.

(57) ABSTRACT

A process for removing one or more unsaturated halocarbons from a halocarbon mixture comprising one or more unsaturated halocarbons and one or more saturated halocarbons, which process comprises contacting the halocarbon mixture with a mixture of a solid chemical oxidant and a solid support in the presence of water.

19 Claims, 2 Drawing Sheets

PURIFICATION OF SATURATED HALOCARBONS

CROSS REFERENCE TO RELATED APPLICATIONS

This application is a national stage application based upon International Application No. PCT/GB02/01544, filed Mar. 28, 2002, which claims priority from Great Britain Application No. GB 0107705.6, filed Mar. 28, 2001.

This invention relates to a process for removing one or more unsaturated halocarbon by-products from one or more saturated halocarbons.

Saturated halocarbons are prepared on an industrial scale by a number of known processes. For example, hydrofluorocarbons may be prepared by reaction of hydrochlorocarbons with hydrogen fluoride in the presence of a chromium containing catalyst.

Many of the processes currently used to prepare saturated halocarbons produce unsaturated halocarbon by-products as well as the desired saturated halocarbon product. For example, in the process for the preparation of 1,1,1,2-tetrafluoroethane (R-134a), 1-chloro-2,2-difluoroethene (A1122) and cis and/or trans 1-chloro-1,2-difluoroethene (A1122a) are typically produced. In the process for the preparation of 1,1,1,3,3-pentafluoropropane (R-245fa), 1-chloro-3,3,3-trifluoropropene (A1233zd) is typically produced. In the process for the preparation of 2,2-dichloro-1,1,1-trifluoroethane (R-123), 1,1-dichloro-2,2-difluoroethene (A1112a), chlorotrifluoroethene (A113), 2-chloroperfluorobutene-2 and 2-chloro-1,1,1,4,4,4-hexafluorobutene-2 are typically produced. In the process for the preparation of 1,1,1,2,3,3,3-heptafluoroethane (R-227ea), hexafluoropropene (A1216), 1,1,1,3,3-pentafluoropropene (A1225zc) and perfluorobutene-2 (A1318) are typically produced.

Although processes for preparing saturated halocarbons may be modified so as to reduce the level of unsaturated halocarbon by-products produced, it is not possible to prevent the formation of unsaturated halocarbon by-products completely. Thus, in order to provide saturated halocarbon products of adequate purity it is necessary to remove unsaturated halocarbon by-products from saturated halocarbon products.

Several methods for removing unsaturated halocarbon by-products from saturated halocarbons are known.

For example, unsaturated halocarbon by-products such as A1122 and 1-chloro-2-fluoroethene (A1131) may be removed from saturated halocarbon products using a specific molecular sieve, such as AW500 supplied by Union Carbide. However, this molecular sieve is ineffective at removing 1,1,1,2-tetrafluoroprop-2-ene (A1234yf), 1,1,1-trifluoroprop-2-ene (A1243zf) and cis and trans 1-chloro-1,2-difluoroethene (A1122a) by-products.

Unsaturated halocarbon by-products can also be removed from saturated halocarbons by chemical oxidation. For example, an aqueous alkaline solution of potassium permanganate may be used to oxidise unsaturated halocarbon by-products. For example, JP-A-7330640 describes a process for removing 1,1-dichloroethylene (R-1130a) from 1,1-dichloro-1-fluoroethane (R-141b), which comprises contacting a mixture of 1,1-dichloro-1-fluoroethane and 1,1-dichloroethylene with an aqueous solution of a metal permanganate and a metal hydroxide.

EP-A-0357328 describes a process for removing unsaturated halocarbon impurities from 2,2-dichloro-1,1,1-trifluoroethane. The process comprises contacting crude 2,2-dichloro-1,1,1-trifluoroethane with an aqueous alkaline metal permanganate solution.

CA-A-2028879 describes an alternative process for removing unsaturated halocarbons. In the process of CA-A-2028879, halogenated hydrocarbons are contacted with a solid oxidant in the presence of a concentrated acid. Compounds such as polychlorinated biphenyls can be removed using this process.

U.S. Pat. No. 6,077,982 describes a further process for removing unsaturated halocarbons. In the process of U.S. Pat. No. 6,077,982, 1,1,1,3,3-pentafluoroethane (R-245fa) is contacted with chlorine in the presence of ultraviolet light having a wavelength of between 300 and 400 nm, to remove 1-chloro-3,3,3-trifluoropropene (A1233zd).

The known processes for removing unsaturated halocarbons from saturated halocarbon products typically work with specific unsaturated halocarbons only. Conventional aqueous oxidants such as metal permanganates have been shown to be ineffective at removing many unsaturated halocarbon by-products. Additionally, the saturated halocarbon product must be separated from the aqueous oxidants and then dried. The spent aqueous oxidant must also be disposed of. It is typically more difficult to dispose of a spent aqueous oxidant than a spent solid oxidant. Additionally, handling, storage and transportation of liquid oxidants is typically more difficult than for solids.

Thus, there is a need for an improved process for removing unsaturated halocarbons from saturated halocarbons which is simple, industrially applicable and effective for a wide range of unsaturated and saturated products.

The present invention provides a process for removing one or more unsaturated halocarbon by-products from one or more saturated halocarbon products. In other words, the present invention provides a process for purifying one or more saturated halocarbons.

The process of the present invention is an oxidation process, which uses a solid chemical oxidant, a solid support and water only. No further reagents are essential.

However, the oxidation process of the invention will not occur if either the chemical oxidant or the solid support is used alone.

According to the present invention there is provided a process for removing one or more unsaturated halocarbons from a halocarbon mixture comprising one or more unsaturated halocarbons and one or more saturated halocarbons, which process comprises contacting the halocarbon mixture with a mixture of a solid chemical oxidant and a solid support in the presence of water.

The process of the present invention provides a relatively high efficiency of unsaturated halocarbon removal and works with a range of saturated and unsaturated halocarbons.

Typically, the process of the present invention removes unsaturated halocarbons at levels up to 1000 ppm. For example, the process can significantly reduce levels of halogenated propenes originally present at up to 100 ppm.

The use of a solid oxidant in the process of the present invention facilitates separation of the purified saturated halocarbon product from the spent oxidant. In contrast, liquid oxidants are more difficult to separate from the saturated halocarbon product. Additionally, it is easier to dispose of a spent solid oxidant compared to a spent liquid oxidant. It is also easier to handle and transport solid oxidants compared to liquid oxidants.

BRIEF DESCRIPTION OF THE DRAWING

In the course of the description to follow, reference will be made to the attached drawings in which.

DESCRIPTION OF THE PREFERRED EMBODIMENTS

Figure 1:
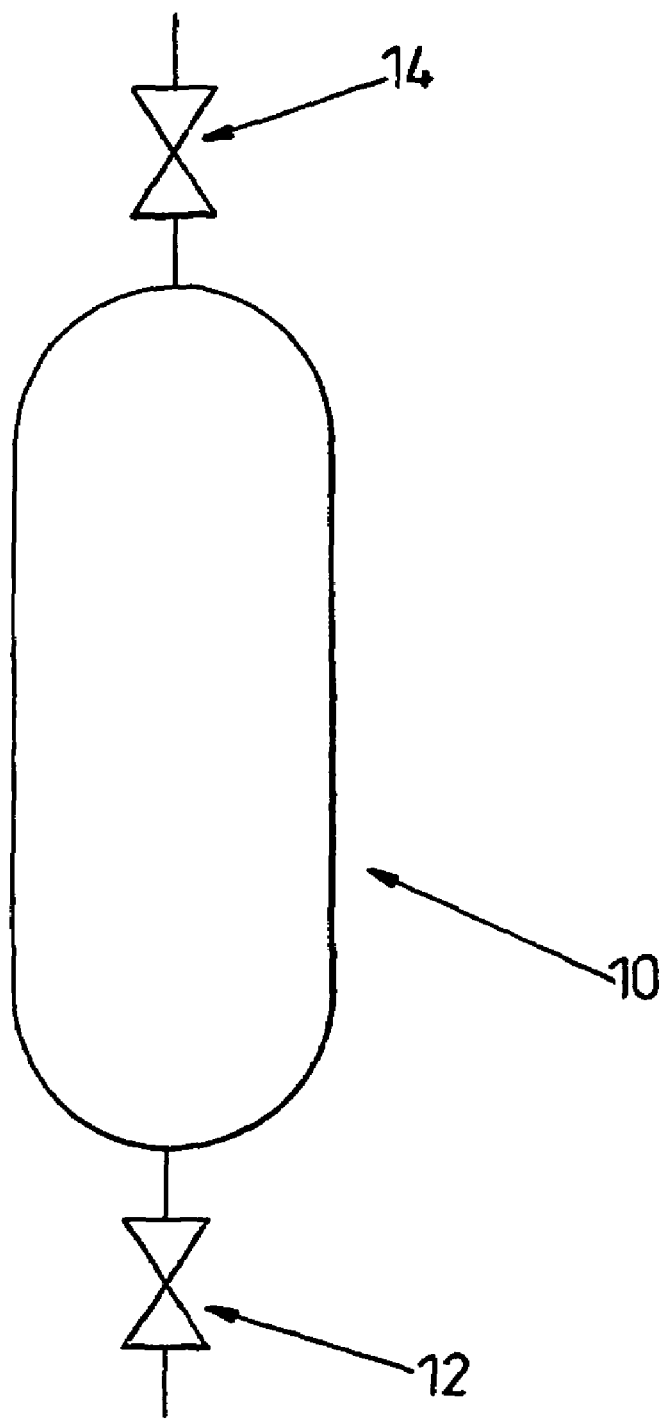
FIG. 1 shows apparatus used for stagnant tests to be described herein.

By the term "halocarbon" we mean compounds that contain carbon, halogen atoms such as chlorine, fluorine, bromine and iodine and, optionally, hydrogen in their structure.

The saturated halocarbons that may be purified using the process of the present invention include saturated hydrofluorocarbons, saturated hydrochlorocarbons, saturated hydrochlorofluorocarbons, saturated chlorofluorocarbons, saturated perchlorocarbons and saturated perfluorocarbons.

Preferably, the process of the present invention is used to purify saturated hydrofluorocarbons, saturated hydrochlorocarbons or saturated hydrochlorofluorocarbons. More preferably, the saturated halocarbon that may be purified using the process of the present invention is a saturated hydrofluorocarbon or a saturated hydrochlorofluorocarbon.

By the term "hydrofluorocarbon" we mean compounds that contain only carbon, hydrogen and fluorine in their structure. By the term "hydrochlorocarbon" we mean compounds that contain only carbon, hydrogen and chlorine in their structure. By the term "hydrochlorofluorocarbon" we mean compounds that contain only carbon, hydrogen, chlorine and fluorine in their structure. By the term "chlorofluorocarbon" we mean compounds that contain only carbon, chlorine and fluorine in their structure. By the term "perchlorocarbon" we mean compounds that contain only carbon and chlorine in their structure. By the term "perfluorocarbon" we mean compounds that contain only carbon and fluorine in their structure.

The saturated halocarbons typically have a carbon chain length of from one to twenty, preferably of from one to six and more preferably of from one to four. Most preferably, the saturated halocarbons have a carbon chain length of two or three.

The unsaturated halocarbons that can be removed using the process of the present invention include unsaturated hydrofluorocarbons, unsaturated hydrochlorocarbons and unsaturated hydrochlorofluorocarbons.

The unsaturated halocarbons typically have a carbon chain length of from two to twenty, preferably of from two to six. Most preferably, the unsaturated halocarbons have a carbon chain length of two or three.

It is particularly preferred that the saturated halocarbon which may be purified using the process of the present invention is 1,1,1,2-tetrafluoroethane (R-134a), pentafluoroethane (R-125), 1,1,1-trifluoroethane (R-143a), difluoromethane (R-32), 1,1,1,3,3-pentafluoropropane (R-245fa) or 1,1,1,2,3,3,3-heptafluoropropane (R-227ea). When the saturated halocarbon is 1,1,1,2-tetrafluoroethane, the unsaturated halocarbons that are removed using the process of the present invention typically include 1,1,1,2-tetrafluoroprop-2-ene (A1234yf), 1,1,1-trifluoroprop-2-ene (A1243zf) and 1-chloro-1,2-difluoroethene (A1122a). Other unsaturated halocarbons typically removed using the process of the present invention include 1-chloro-2-fluoroethene (A1131), 1-chloro-2,2-difluoroethene (A1122), 1-chloro-3,3,3-trifluoropropene (A1233zd), 1,2-dichloro-1,2-difluoroethene (A1112), 1,1-dicloro-2,2-difluoroethene (A112a), chlorotrifluoroethene (A113), hexafluoropropene (A1216), 1,1,1,3,3-pentafluoropropene (A1225zc) and perfluorobutene-2 (A1318). For example, A1122 is typically removed from R-134a using the process of the invention.

Suitable solid chemical oxidants for use in the present process include alkali metal and alkaline earth metal permanganates. A particularly preferred solid chemical oxidant is potassium permanganate.

The solid chemical oxidant is supported on a solid support. The solid support may be basic. For example, it is preferred that the solid support is basic when potassium permanganate is used as the oxidant.

Suitable solid supports for use in the present process include soda lime, lime and quicklime. A preferred solid support is sodalime that has a low potassium hydroxide content. This is because a high content of potassium hydroxide may cause hydrogen fluoride to be removed from the saturated halocarbon product to produce unwanted unsaturated by-products.

The ratio of the solid support to the solid chemical oxidant may be any ratio up to the saturation limit of the oxidant on the support and is preferably about 10:1 by weight.

The mixture of the solid chemical oxidant and the solid support may be prepared by any suitable method. For example, this mixture may be prepared by simple mixing of the chemical oxidant and the support in the solid phase. Alternatively, a solution of the chemical oxidant may be impregnated onto the support and the resulting mixture heated to dryness. Any suitable method of impregnation known to a person skilled in the art could be used.

When the mixture of the solid chemical oxidant and the solid support is formed by impregnation, an aqueous solution of the chemical oxidant is preferably impregnated onto the solid support.

Typically, a greater loading of the chemical oxidant on the solid support is achieved when the mixture of the solid chemical oxidant and the solid support is prepared by impregnation of a solution of the chemical oxidant onto the solid support and then heating and stirring the resultant mixture.

The process of the present invention comprises contacting the mixture of the solid chemical oxidant and the solid support with the halocarbon mixture comprising one or more unsaturated halocarbons and one or more saturated halocarbons in the presence of water to produce one or more saturated halocarbons that are substantially free of unsaturated halocarbons.

In the process of the invention, the halocarbon mixture may be contacted with the mixture of the solid chemical oxidant and the solid support in either the liquid or the vapour phase. Whether the halocarbon is contacted with the mixture of the solid chemical oxidant and the solid support in either the liquid or the vapour phase may depend upon the manufacturing process that is used to produce the halocarbon. For example, if the saturated halocarbon is produced in the liquid phase, then it will typically be preferred to conduct the process of the present invention with the saturated halocarbon in the liquid phase. Similarly, if the saturated halocarbon is produced in the vapour phase, it will typically be preferred to conduct the process of the present invention with the saturated halocarbon in the vapour phase.

When the halocarbon mixture is contacted with the mixture of the solid chemical oxidant and the solid support in the liquid phase, the reaction residence time is preferably from 5 to 500 minutes, more preferably from 30 to 180 minutes.

When the halocarbon mixture is contacted with the mixture of the solid chemical oxidant and the solid support in the vapour phase, the reaction residence time is preferably from 1 to 500 seconds, more preferably from 30 to 120 seconds.

Preferably, the process of the invention is conducted at ambient temperature or above ambient temperature. By ambient temperature we mean 0 to 30° C. The process of the invention may be conducted at a temperature of up to 100° C.

The process of the invention may be conducted at subatmospheric, atmospheric or superatmospheric pressure.

In order for the oxidation reaction to occur in the process of the present invention, it is essential that it is conducted in the presence of water. The water may be present in either the liquid or the vapour phase.

It is preferred, but not essential, that the water is present in the liquid phase if the saturated halocarbon is in the liquid phase and that the water is present in the vapour phase if the saturated halocarbon is present in the vapour phase.

The water may be present in the halocarbon mixture and/or in the solid oxidant and/or in the solid support.

The present invention is now illustrated but not limited with reference to the following examples.

EXAMPLE 1

Preparation of Doped R-134a Mixture

A sample of pure R-134a was doped with a number of unsaturated halocarbon impurities to provide a doped R-134a mixture as shown in Table 1.

TABLE 1

Composition of doped R-134a mixture

| Unsaturated halocarbon | Amount present (ppm) |
|---|---|
| A1234yf | 14 |
| A1243zf | 9 |
| c-A1122a | 6 |
| t-A1122a | 1 |
| A1122 | 18 |

EXAMPLE 2

Preparation of Potassium Permanganate/Soda Lime Mixtures

Solid state potassium permanganate/soda lime mixtures were prepared according to methods (a) and (b).

Method (a)

Solid $KMnO_4$ (1 g) in the form of fine crystals was mixed with dried granular solid soda lime (10 g) in a Whitey bomb (250 ml) to produce a 10% mixture of $KMnO_4$ supported on the soda lime. The Whitey bomb was then vigorously agitated on a mechanical shaker for several hours, usually overnight (i.e. from 16 to 18 hours).

Method (b)

Dried soda lime granules (50 g) were added to a solution of $KMnO_4$ (10 g) in warm water (50 ml) in an evaporating dish. The resulting mixture was heated to dryness with constant stirring and then transferred to a Pye-Unicam oven set at 300° C. for further drying for about 2 hours.

EXAMPLE 3

Removal of Unsaturated Halocarbons from a Liquid Stream

Two stagnant tests were conducted in order to investigate the effectiveness of the potassium permanganate/soda lime mixtures prepared according to method (a) of Example 2 at removing unsaturated halocarbons from the doped R-134a mixture prepared according to Example 1 in the liquid phase.

FIG. 1 shows the apparatus used for the stagnant tests. The apparatus used comprises a Whitey bomb (10). The Whitey bomb comprises two valves (12, 14).

A $KMnO_4$/soda lime mixture (comprising 1.3 g $KMnO_4$ and 10.5 g pre-dried soda lime) was prepared according to method (a) of Example 2 and placed in a Whitey bomb (10) having an internal volume of 250 ml. The Whitey bomb (10) was then partially evacuated, cooled in liquid nitrogen for at least 20 seconds and a doped R-134a mixture (131 g) mixture prepared according to Example 1 was added via. valve (12). The Whitey bomb (10) was then placed on an electric shaker and shaken vigorously for 21 hours. Samples (20 ml) from the headspace in the bomb were taken via. valve (14) at 1, 2, 3, 4 and 21 hours and analysed using gas chromatography immediately.

The gas chromatography results showed no change in the levels of the unsaturated halocarbon impurities in the doped R-134a mixture after 21 hours.

The previous method was repeated using a $KMnO_4$/soda lime mixture comprising wet soda lime (55 g) containing about 2 to 12% water and $KMnO_4$ (10 g). A total of about 0.2 ml of water was injected into the mixture whilst it was shaken. The wet $KMnO_4$/soda lime mixture was placed in a Whitey bomb (10) having an internal volume of 250 ml. The Whitey bomb (10) was then partially evacuated, cooled in liquid nitrogen for at least 20 seconds and a doped R-134a mixture (121 g) prepared according to Example 1 was added via. valve (12). The Whitey bomb (10) was shaken vigorously for a total of 72 hours. Samples (20 ml) of the headspace in the bomb were taken via. valve (14) after 0.5 and 72 hours and analysed using gas chromatography immediately.

The gas chromatography results showed that almost all of the unsaturated halocarbon impurities had been removed after 72 hours (only about 10% of A1234yf remained).

The results show that a simple mixture of solid potassium permanganate and solid soda lime, in the presence of water, will remove unsaturated halocarbons from a liquid mixture of unsaturated and saturated halocarbons. The presence of water is essential for the process to work.

EXAMPLE 4

Removal of Unsaturated Halocarbons from a Vapour Stream

A series of flow system tests were conducted in order to investigate the effectiveness of the potassium permanganate/soda lime mixtures prepared according to method (b) of Example 2 at removing unsaturated halocarbons from the doped R-134a mixture prepared according to Example 1 in the vapour phase. The potassium permanganate/soda lime mixture was prepared according to method (b) of Example 2 in order to maximise the percentage of the potassium permanganate supported on the soda lime structure.

Figure 2:
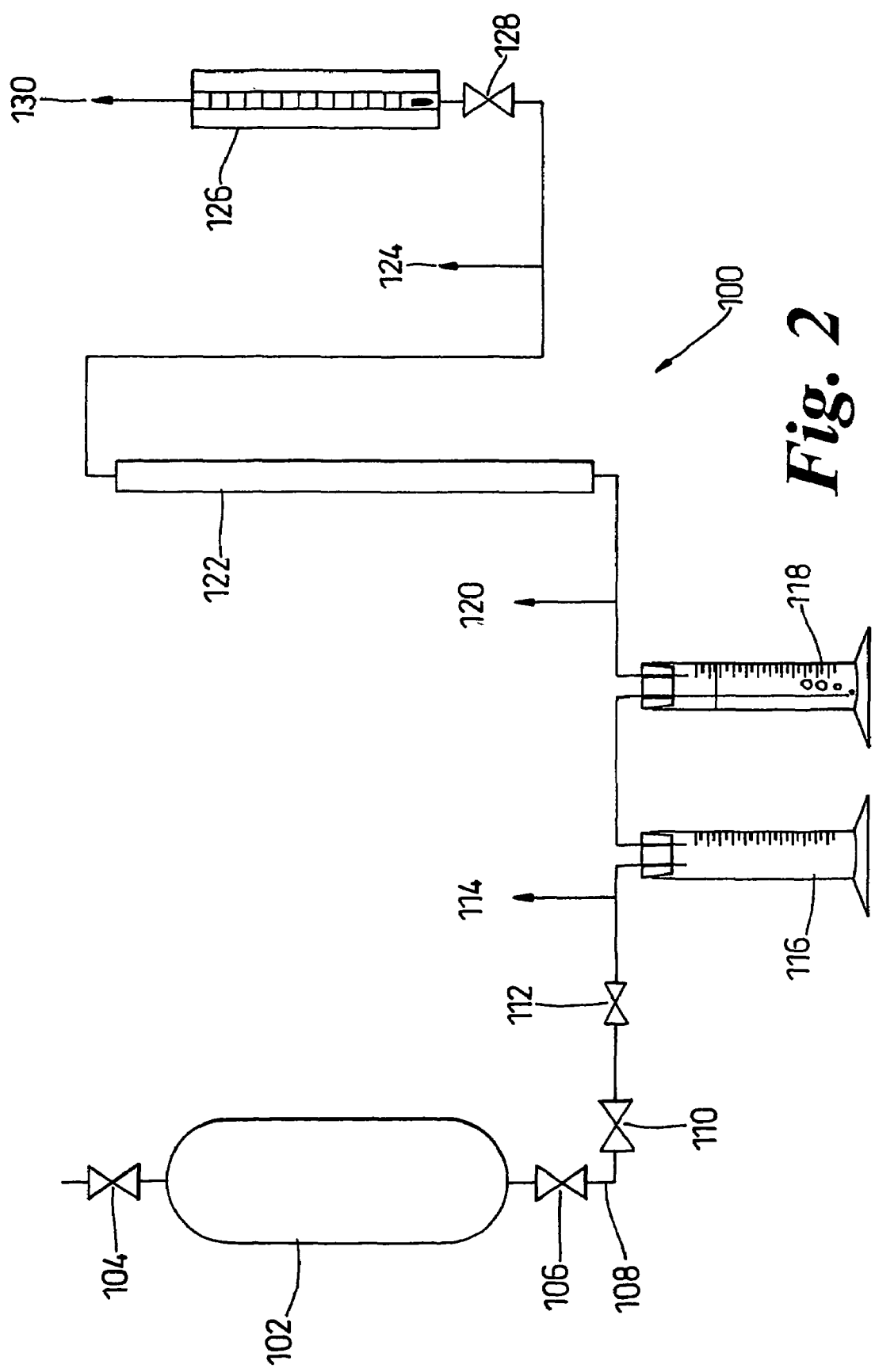
FIG. 2 shows apparatus used for flow system tests to be described herein.

FIG. 2 shows the apparatus (100) used for the flow system tests. The apparatus (100) comprises a Sample bomb (102) having an inlet valve (104) and an outlet valve (106). A gas line (108) extends from the outlet valve (106). Both a pressure let-down valve (110) and a needle valve (112) are positioned on the gas line (108). Downstream of the needle valve (112) are positioned a lute (114), a catch pot (116), a water saturator (118) and a first sample point (120). Downstream of the first sample point (120) is a glass column (122). A second sample point (124) and a rotameter (126) are located downstream of the glass column (122). The rotameter (124) has an inlet valve (128) and a vent (130) to the atmosphere.

Flow Test (i)

A $KMnO_4$/soda lime mixture was prepared according to method (b) of Example 2. Pre-dried soda lime (50 g) was dissolved in a warm solution containing $KMnO_4$ (10.2 g) in water (50 ml). The mixture was constantly stirred whilst heating until all the water had evaporated. The dried mixture was then placed in an oven at 300° C. for 2 hours. The mixture was sieved through a 500 μm sieve in order to remove fines (i.e. particulate matter typically smaller than 500 μm in size) before charging the mixture into a glass column (122) of the apparatus (100) shown in FIG. 2.

The doped R-134a mixture was placed in the Sample bomb (102) and bubbled through a water saturator (118) at a vapour rate of from 50 to 55 ml/min and then through the glass column (122) containing the $KMnO_4$/soda lime mixture. "Off gas" samples were taken over a period of between 1 and 53 hours from the second sample point (124) shown in FIG. 2. The samples taken were analysed by gas chromatography immediately.

No unsaturated halocarbons had been removed from the doped R-134a mixture after 1 hour. The majority of the unsaturated halocarbons had been removed with only 10% of the A1234yf remaining after 53 hours.

Flow test (i) shows that unsaturated halocarbons can be removed from a vapour stream using soda lime impregnated with potassium permanganate.

Flow Test (ii)

Flow test (i) was repeated but the flow rate of the doped R-134a was varied. The aim of this test was to observe the effect of varying the residence time on the level of unsaturated halocarbons removed.

The flow rate of the doped R-134a mixture was varied from 35 to 80 ml/min with samples taken at 1 hour intervals after each change and analysed by gas chromatography immediately. The results are shown in Table 2 below.

TABLE 2

Results of flow test (ii)

| R-134a flow rate (ml/min) | Results |
| --- | --- |
| 35 | Complete removal of unsaturated halocarbons |
| 40 | Approx. 7% A1234yf remained |
| 50 | Approx. 10% A1234yf remained |
| 60 | Approx. 16% A1234fy and 8% A1243zf remained |
| 70 | Approx. 30% A1234yf and 18% A1243zf remained |
| 80 | Approx. 40% A1234yf and 22% A1243zf remained |

Flow test (ii) shows that unsaturated halocarbons can be removed from a vapour stream using soda lime impregnated with potassium permanganate. The most efficient removal of unsaturated halocarbons was achieved using a flow rate of 35 ml/min.

Flow Test (iii)

Flow test (i) was repeated but the water content in the $KMnO_4$/soda lime mixture was altered.

This test was conducted in order to observe changes in the levels of the unsaturated halocarbons whilst altering the amount of water present in the $KMnO_4$/soda lime mixture.

The $KMnO_4$/soda lime mixture was prepared in the same manner as for test (i), except that the mixture was dried for only 1 hour prior to charging to the column.

The doped R-134a mixture was passed directly to the bed and samples were taken over a 3 hour period. The flow was then routed through the water saturator and samples were taken at 0.5, 1.5, 3 and 4 hours and analysed by gas chromatography immediately. Finally the flow was re-directed to the column (after the bed was dried in an oven to speed up effect of no water present). More samples were taken at 1, 2 and 3 hours and analysed by gas chromatography immediately. The results are shown in Table 3 below.

TABLE 3

Results of flow test (iii)

| Amount of water | Time (hours) | Results |
| --- | --- | --- |
| No water | 3 | Only A1122 partially removed |
| With water | 4 | 0% A1122, 35% A1234yf, 26% A1243zf, 0% c1122a and 0% t1122a remained |
| No water | 3 | 55% A1122, 81% A1234yf, 66% A1243zf, 32% c1122a and 0% t1122a remained |

Flow test (iii) shows that water must be present in order for unsaturated halocarbons to be removed from a vapour stream using soda lime impregnated with potassium permanganate.

Flow tests (i) to (iii) show that the moisture taken up by the vapour stream is sufficient to enable the oxidation reaction to occur.

The order of ease of removal of the unsaturated halocarbons was shown to be A1122>trans A1122a>cis A1122a>A1243zf>A1234yf.

A greater loading of the potassium permanganate on the soda lime was achieved when the $KMnO_4$/soda lime mixture was prepared in solution (i.e. according to method (b) of Example 2).

The invention claimed is:

1. A process for removing one or more unsaturated halocarbons from a halocarhon mixture comprising one or more unsaturated halocarbons and one or more saturated halocarbons, which process comprises contacting the halocarbon mixture with a mixture of a solid chemical oxidant and a basic solid support in the presence of water.

2. A process according to claim 1, wherein the at least one saturated halocarbon is a saturated hydrofluorocarbon, a saturated hydrochlorofluorocarbon, a saturated chlorofluorocarbon, a saturated perchlorocarbon or a saturated perfluorocarbon.

3. A process according to claim 1, wherein the at least one saturated halocarbon is a saturated hydrofluorocarbon or a saturated hydrochlorofluorocarbon.

4. A process according to claim 1, wherein the at least one saturated halocarbon has a carbon chain length of from one to four.

5. A process according to claim 1, wherein the at least one unsaturated halocarbon is an unsaturated hydrofluorocarbon, an unsaturated hydrochlorocarbon or an unsaturated hydrochlorofluorocarbon.

6. A process according to claim 1, wherein the at least one unsaturated halocarbon has a carbon chain length of two or three.

7. A process according to claim 1, wherein the at least one of the saturated halocarbons is 1,1,1,2-tetrafluoroethane (R-134a), pentafluoroethane (R-125), 1,1,1-trifluoroethane (R-143a), difluoromethane (R-32), 1,1,1,3,3-pentafluoropropane (R-245fa) or 1,1,1,2,3,3,3-heptafluoropropane (R-227ea).

8. A process according to claim 7, wherein the at least one of the unsaturated halocarbons is 1,1,1,2-tetrafluoroprop-2-ene (A1234yf), 1,1,1-trifluoroprop-2-ene (A1243zf), cis and/or trans 1-chloro-1,2-difluoroethene (A1122a), 1-chloro-2-fluoroethene (A1131), 1-chloro-2,2difluoroethene (A1122), 1-chloro-3,3,3-trifluoropropene (A1233zd), 1,2-dichloro-1,2-difluoroethene (A1112), 1,1-dichloro-2,2-difluoroethene (A1112a), chlorotrifluoroethene (A1113), hexafluoropropene (A1216), 1,1,1,3,3-pentafluoropropene (A1225zc) or perfluoro-butene-2 (A1318).

9. A process according to claim 1, wherein the solid chemical oxidant is an alkali metal or alkaline earth metal permanganate.

10. A process according to claim 9, wherein the solid chemical oxidant is potassium permanganate.

11. A process according to claim 1, wherein the solid support is a soda time.

12. A process according to claim 1, wherein the ratio of the solid support to the solid chemical oxidant is any ratio up to the saturation limit of the oxidant on the support.

13. A process according to claim 1, which is carried out in the liquid or the vapour phase.

14. A process according to claim 13, which is carried out in the liquid phase and the reaction residence time is from 5 to 500 minutes.

15. A process according to claim 13, which is carried out in the vapour phase and the reaction residence time is from 1 to 500 seconds.

16. A process according to claim 1, which is conducted at a temperature of from 0 to 100° C.

17. A process according to claim 1, which is conducted at a subatmospheric, atmospheric or superatmospheric pressure.

18. A process according to claim 1, wherein the mixture of a solid chemical oxidant and a solid support is provided by mixing the solid chemical oxidant with the solid support.

19. A process according to claim 1, wherein the mixture of a solid chemical oxidant and a solid support is provided by impregnation of a solution of the chemical oxidant onto the solid support and then heating the resulting mixture to dryness.

* * * * *